United States Patent
Chan et al.

(10) Patent No.: US 6,627,435 B2
(45) Date of Patent: Sep. 30, 2003

(54) PERFUSION INCUBATOR

(75) Inventors: Paul Chan, Queensland (AT); Allan Joseph Hilling Smith, Queensland (AT); David Michel, Queensland (AT)

(73) Assignees: William A. Cook Australia Pty. Ltd., Queensland (AU); Cook Incorporated, Bloomington, IN (US)

(*) Notice: Subject to any disclaimer, the term of this patent is extended or adjusted under 35 U.S.C. 154(b) by 12 days.

(21) Appl. No.: 09/819,407

(22) Filed: Mar. 28, 2001

(65) Prior Publication Data

US 2001/0039045 A1 Nov. 8, 2001

(30) Foreign Application Priority Data

Mar. 28, 2000 (AT) .............................. PQ 6530

(51) Int. Cl.⁷ .............................. C12M 3/00; C12N 5/02
(52) U.S. Cl. .................. 435/293.1; 435/293.2; 435/305.1; 435/305.2; 435/325
(58) Field of Search ............ 435/383, 325, 435/289.1, 292.1, 293.2, 305.1–305.4, 288.3, 288.4, 288.7, 303.1

(56) References Cited

U.S. PATENT DOCUMENTS

| | | | |
|---|---|---|---|
| 3,426,444 A | * | 2/1969 | Dews et al. ............... 34/218 |
| 4,311,798 A | | 1/1982 | Katinger et al. |
| 4,435,508 A | | 3/1984 | Gabridge |
| 4,530,907 A | | 7/1985 | Peterson et al. |
| 4,665,033 A | | 5/1987 | Buchwalder |
| 4,774,187 A | | 9/1988 | Lehmann |
| 4,814,278 A | | 3/1989 | Hamamoto et al. |
| 5,139,951 A | | 8/1992 | Butz et al. |
| 5,443,985 A | | 8/1995 | Lu et al. |
| 5,496,697 A | * | 3/1996 | Parce et al. ................. 435/29 |
| 6,268,121 B1 | * | 7/2001 | Takeshita et al. ........... 204/400 |

FOREIGN PATENT DOCUMENTS

EP          0171896          2/1986

* cited by examiner

*Primary Examiner*—William H. Beisner
(74) *Attorney, Agent, or Firm*—Brinks Hofer Gilson & Lione

(57) ABSTRACT

A perfusion incubator having a fluid conditioning unit (12), a well assembly (7) and a well assembly heating unit (14), a peristaltic pump (4) and a fluid collection unit (11). The well assembly has a number of wells (20, 21) each having a transparent lid (30) and a fluid inlet (26) and a fluid outlet (27). An illumination device (13) is under the well so that the cell being cultured in the well assembly can be observed by means of a microscope (15). Each fluid inlet (26) is positioned so as to allow a tangential entry of fluid to the well at a mid point in the well, and each fluid outlet (27) is above the fluid inlet with the cell to be cultured in a lower portion of the well so that flow of fluid in the well is formed into a vortex which tends to draw fluid from around the cell without direct flow over the embryo.

18 Claims, 4 Drawing Sheets

PERFUSION INCUBATOR

RELATED APPLICATION INFORMATION

This application claims priority from Australian Provisional Application Ser. No. PQ 6530 filed Mar. 28, 2000.

1. Technical Field

This invention relates to incubators and more particularly incubators for cell culturing, in particular culturing embryos of mammalian species.

2. Background of the Invention

Some cells growing in a liquid medium produce exogenous and growth factors which surround the cell in the liquid medium. In the growing of such cells in vitro it is important not to immediately flush these exogenous and growth factors when changing the medium around the cell.

It is the object of this invention to provide an incubator well for the growing of cells such as embryos which have favorable growing conditions.

SUMMARY OF THE INVENTION

The invention is said to reside in a perfusion incubator, including a fluid supply, a fluid conditioning unit, at least one well assembly and a well assembly heating unit, a pump such as a peristaltic pump, and preferably a fluid collection unit, the well assembly including at least one well, each well having a fluid inlet and a fluid outlet, each fluid inlet being positioned at a point in the well above the cell and each fluid outlet being positioned above its respective fluid inlet above the cell (such as an embryo) to be cultured in a lower portion of the well, the fluid inlet connected to the fluid supply and the fluid outlet connected to the fluid collection unit via the peristaltic pump whereby on the placing of the specimen cell to be cultured in each well and flowing fluid through the well, culturing of the cell can occur.

There may be further included an illumination device so that the cell being cultured in the well assembly can be observed by means of a microscope. There may be further included a microscope mount associate with the perfusion incubator.

Each well may include means to provide a flow path from the fluid inlet to the fluid outlet within the well so that fluid flow is not directly around the cell in the well.

Preferably, each fluid inlet is positioned so as to allow a tangential entry of fluid to the well at a mid point in the well, and the fluid outlet being positioned above the fluid inlet with the cell to be cultured in a lower portion of the well, whereby flow of fluid in the well is formed by this construction into a vortex which will tend to draw fluid from around the cell without direct flow over the cell.

Each well can have a stepped side wall defining an upper chamber and a smaller lower chamber with a lid which in use is adapted to extend partially into the upper chamber.

Each lid may be made of a substantially transparent material so as to allow for viewing of the cell in the lower chamber.

The well assembly may be transparent so that the cell can be illuminated from below.

The peristaltic pump can provide a flow rate of fluid through each well of between 40 microliters per hour up to 4000 microliters per hour when in flush mode.

The fluid conditioning unit may be operated at a temperature of approximately 0.5° C. above the operating temperature of the well assembly heating unit whereby increase in solubility of gases in the fluid because of the 0.5° C. temperature drop upon entry into a well, and decrease in solubility because of reduced pressure in the well due to suction of the peristaltic pump, are both compensated for and gas bubbles do not form in the culture well.

In an alternate form the invention is said to reside in a perfusion incubator well assembly having a body, at least one well in the body, the or each well having a stepped side well defining an upper chamber and a smaller lower chamber and a lid, a fluid inlet to the or each well and fluid outlet from the or each well, the fluid inlet being positioned so as to allow tangential entry of fluid to the well at a lower portion of the upper chamber and the fluid outlet being positioned above the fluid inlet.

A well closure such as a lid may be adapted to extend partially into the upper chamber, and may include an O-ring seal and be made of a substantially transparent material so as to allow viewing of an cell in the lower chamber.

The body may be made from a substantially transparent material so that with illumination from below, the cell being cultured can be viewed.

The fluid inlet and the fluid outlet to the or each well may be formed by apertures formed in the body.

It can be seen, therefore, that by this invention the perfusion incubator is a system which based on the principle of perfusion of specifically designed culture fluid, provides a suitable environment for the production, development and storage of pre-implantation embryos from mammalian species. The system maintains purpose-built culture wells at a pre-set temperature while perfusing carbon dioxide enriched culture media over the cells.

BRIEF DESCRIPTION OF THE DRAWINGS

This very generally describes the invention but to assist with understanding, reference will now be made to the accompanying drawings which show a preferred embodiment of the invention.

DETAILED DESCRIPTION

Figure 1:
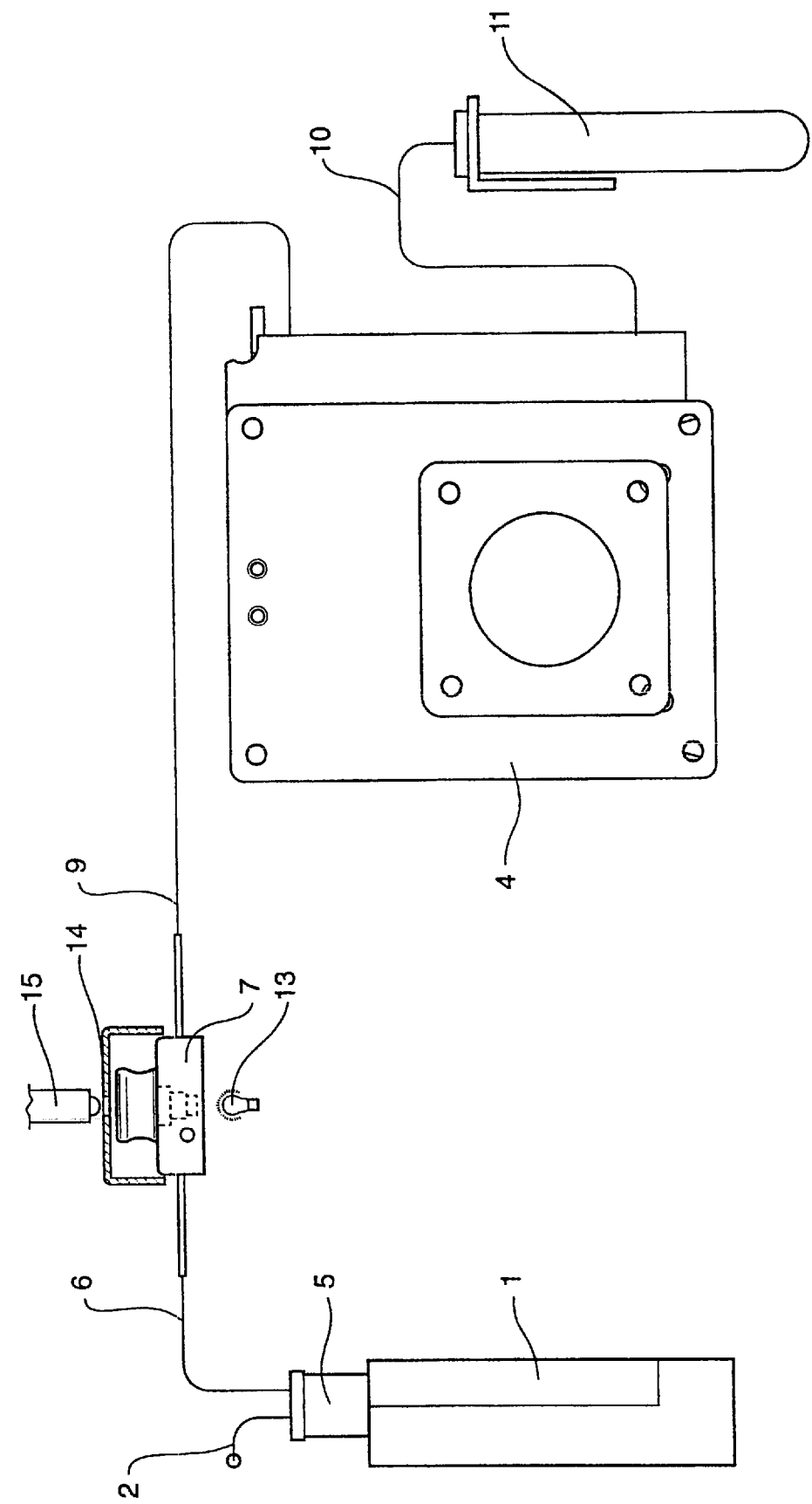
FIG. 1 shows a schematic view of a perfusion incubator according to the present invention.

Now looking at the drawings in detail we see that the perfusion incubator includes a fluid heater unit 1 which has a gas inlet 2, the peristaltic pump 4 draws fluid from test tube 5 in the fluid heater unit through fluid inlet line 6, through the chamber 7 (as will be discussed in detail below) through the fluid outlet line 9 and after the peristaltic pump 4, travels through line 10 into fluid collection unit 11.

Figure 2:
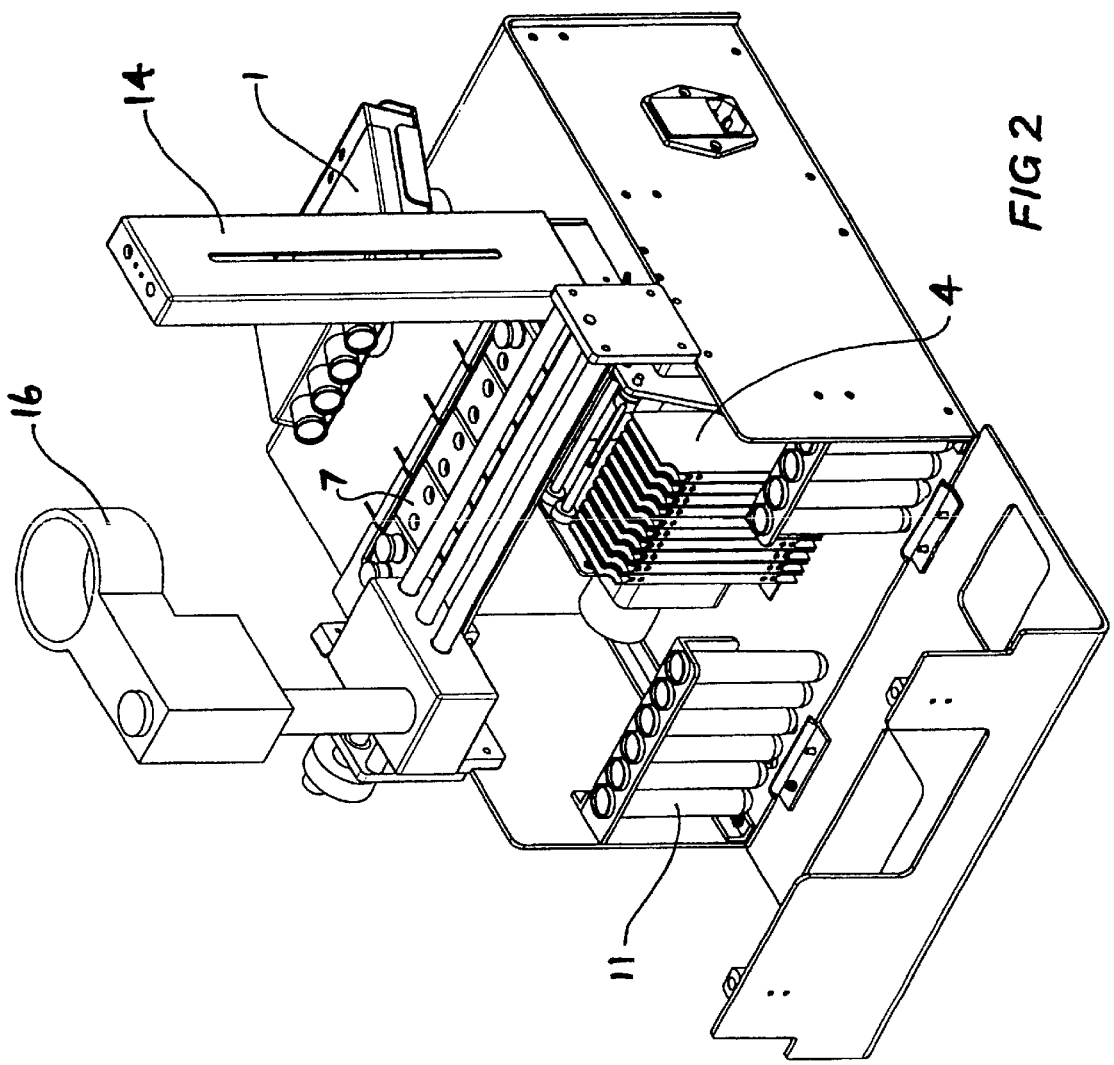
FIG. 2 shows an isometric view of a perfusion incubator.

The fluid flow lines 6, 9, and 10 are not shown in FIG. 2.

Below the chamber 7 is an illumination source 13. Above the chambers is a chamber heater unit 14 and above this is a microscope lens 15. The microscope lens is held in microscope holder 16 as can be seen in FIG. 2. In FIG. 2 the chamber heater unit 14 has been raised so that the chambers below it can be seen.

Figure 3:
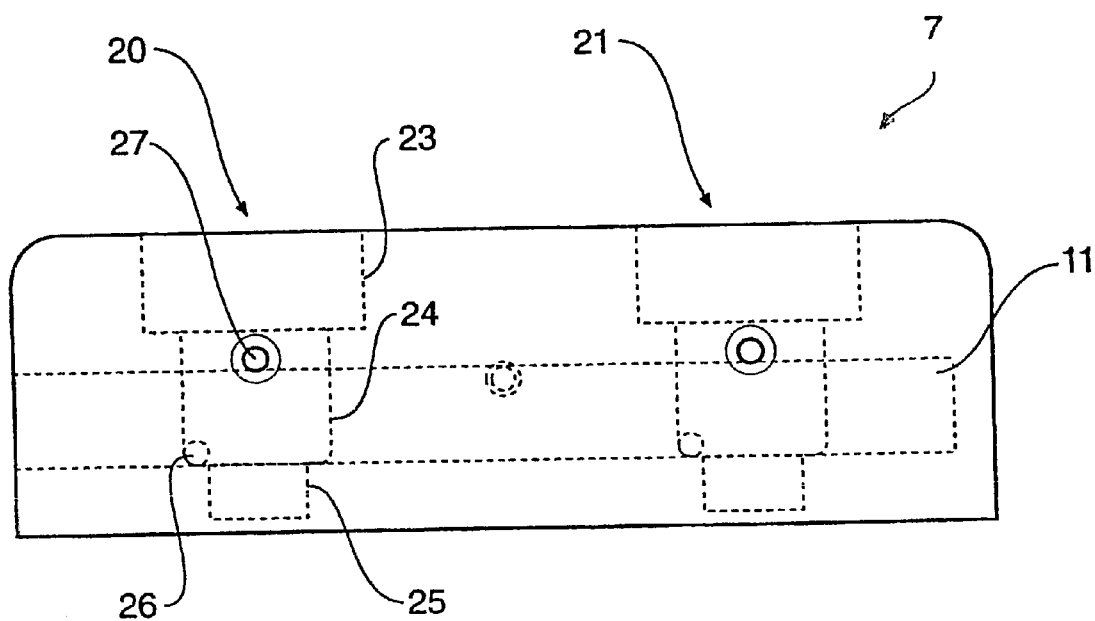
FIG. 3 shows a cross sectional view of a culture chamber for the perfusion incubator.
Figure 4:
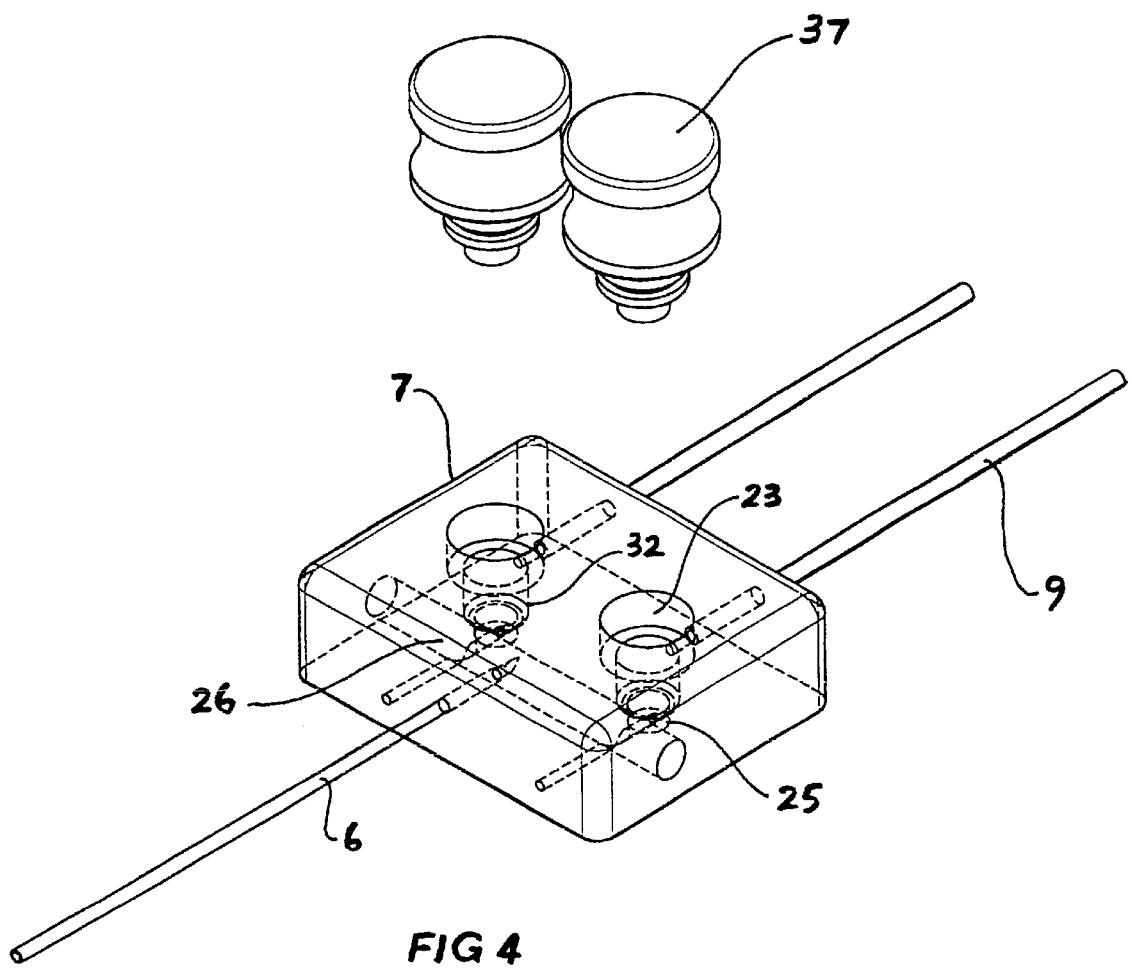
FIG. 4 shows an isometric view of a well assembly.
Figure 5:
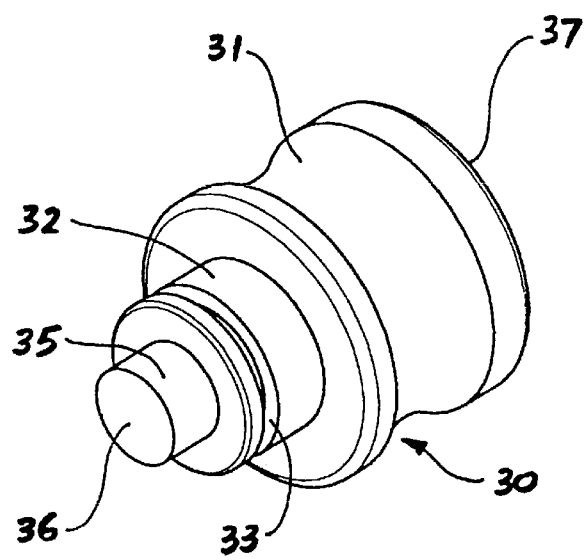
FIG. 5 shows an isometric view of the lid for the culture chamber.

As can be seen in the side view in FIG. 3, the chamber 7 has a first well generally shown as 20 and a second well generally shown as 21. Each well has a stepped cross section with at least two sections generally, and as shown, may have a largest upper section 23 into which the lid fits, a middle section 24 and a smallest lower section 25. The fluid inlet 26 to each well is preferably at the bottom of the middle section 24 and the fluid outlet 27 is preferably at the top of the middle section 24. In use, a cell to be cultured is placed in the lower section 25. The well closure, such as lid 30, as can be seen in FIGS. 4 and 5, has an upper portion 31 to enable placement and removal of the lid and is of a size which can be gripped by the fingers. A central portion 32 of the lid is adapted to fit into the upper section 23 of the well with an O-ring in the slot 33 providing sealing of the lid. The lower portion 35 of the lid is adapted in use to fit into the middle section 24 of the well but allows fluid to flow around it towards the fluid outlet 27. The lower surface 36 of the lid 30 and the upper surface 37 are both finely polished so that viewing through the lid enables viewing of the cell being cultured in the lower section of the well.

The well can have the lid system described, but if an annular region is required to assist with the tangential flow, then a coaxial tube could be fitted in the well, and the lid can be replaced by a simple seal enabling the specimen or cell structure to be positioned in the lower chamber. The sides of the well can be curved if that would improve the tangential flow of the fluid and the formation of the vortex.

In a preferred embodiment, the perfusion incubator according to the invention is constructed and operated as discussed below.

The tube heater will preferably contain at least six tubes containing culture fluid which may or may not be the same as that in other tubes. The fluid or media is held at the user's specified temperature and equilibrated with specific gas mixtures capable of maintaining the required pH in the culture media.

Each pair of culture wells is connected by non-toxic, non-permeable tubing to a tube of media in the front, and to a peristaltic pump in the rear of the culture wells. Whilst it is preferred to use a peristaltic pump, an ordinary continuous pump could alternatively be employed. It could be located in the supply line or the exhaust line, although the latter is preferred. From the peristaltic pump the tubing continues to the media waste receiver tubes, where used media is collected as waste or for further analysis. The peristaltic pump draws solution from the heated reservoirs through the culture wells to the waste containers. The whole process of temperature, light and fluid flow control may be maintained by a microprocessor.

In a preferred embodiment the culture wells themselves may be made of plastic materials such as polycarbonate and have highly polished surfaces. Underneath each culture well is a high output light emitting diode. A set of 5 pairs of culture wells may be contained in a heating block. In operation mode the chamber in the heater until which is contained in the lid, is placed down over the culture wells. In the lid is a clear glass strip. Above the heater block is a microscope holder. With a microscope in place and the light emitting diode beneath the culture well turned on, an operator is able to observe the embryos directly in situ.

It is useful in growing a healthy embryo to observe the growth pattern. A motor driven system to position the microscope over each culture well may be used.

The motor driven system may be provided to position the microscope over each consecutive culture well, for instance, at one minute intervals which would make it possible to accumulate digital time lapse photography of growth patterns of individual embryos in each culture well. The illumination beneath each culture well may one be turned on as required to capture an image. Light output from an LED is specifically in the orange-yellow band to be of low energy but provide high contrast. In addition to this, it is preferable the light emitting source contains no ultra-violet radiation as this may damage the embryos.

Embryos for culture are placed in the bottom of the culture well where they stick in the margin between the horizontal and vertical axes of the lower section. The embryos are not dislodged by the action of culture media flowing across them. Culture media is introduced above the lower section as a tangential flow to the inner surface of the culture well and removed from the top of the well. This creates an upward moving vortex which displaces media in the lower section of the culture well. Without this vortex action, media exchange in the bottom section of the well is by diffusion only, which results in embryo death or at best, embryos with very poor morphology which would not be suitable for implantation. A particular feature of the culture wells is the vortex action to exchange media in the bottom section. This action can be observed by the injection of small amounts of dye and following the fluid path.

The reason that the embryos are not placed directly in the fluid path is that exogenous and growth factors excreted by the embryos would be flushed away immediately. By placing in a lower section where the media exchange rate is less than the true flow rate, then the exogenous and growth factors remain in the proximity of the embryos for at least a short time.

In operation mode, with the lids in place, there is a negative pressure of approximately 1 kPa within the culture well as media is being pulled through by the peristaltic pump. This slight negative pressure may cause outgassing of the dissolved gasses which maintain the pH of the culture media. Henry's Law states that the mass of gas dissolved by a given volume of solvent at a constant temperature is proportional to the pressure of the gas in equilibrium with the solvent. Small bubbles which form in the culture well may isolate embryos from culture media with resultant death of the embryos. These minute bubbles cannot be dislodged at the flow rates used in this device. The flow rate used per well can vary between 40 microliters per hour up to 4000 microliters per hour when in flush mode.

To overcome this bubble problem, media at 0.5° C. above the operating temperature of the culture chamber is equilibrated with gas mixture. As gases dissolve with the liberation of heat the Le Chatelier principle dictates that a rise in temperature will cause a decrease in gas solubility. Equilibrating the culture media at 0.5° C. above the chamber temperature with the gas mixture prior to the media's entry into the culture well, ensures that the increase in solubility because of the 0.5° C. temperature drop and decrease in solubility because of the 1 kPa pressure drop are both compensated for and no gas bubbles form in the culture well. Without the pre-equilibration of the media at the higher temperature, the culture well may not perform effectively.

Once the embryos are ready for implantation they can be perfused with cryo-protectant and the whole block can be frozen in liquid nitrogen.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

What is claimed is:

1. A perfusion incubator well assembly having a body with at least one well therein,
   the well having an upper section and a lower section, the latter serving to receive a specimen to be cultured, and a part for permitting the specimen to be positioned in the well; wherein
   the well has a fluid inlet for permitting fluid to enter the well at a location above the position at which the specimen is to be located,
   the well also having a fluid outlet positioned above the fluid inlet,
   the well having a substantially unobstructed lower section; and wherein
   either the inlet or the shape of the well, or both, ensure tangential flow of the fluid.

2. The assembly according to claim 1, wherein the upper section has an annular region for containing the said tangential flow.

3. The assembly according to claim 2, wherein the said part is a sealable lid for the well, and wherein the lid has a portion extendable into the well to form the said annular region, and/or wherein the inlet and/or outlet are formed by apertures in the body.

4. The assembly according to claim 3, wherein the upper part of the lid and the lower part of the said portion are of transparent material, and/or wherein the body in the region of the specimen location is of transparent material, said transparent material enabling observation of the specimen.

5. The assembly according to claim 3, wherein the or each well has a stepped side wall defining the upper section and the lower section which is smaller than the upper section.

6. The assembly according to claim 1, wherein the said inlet is positioned so as to allow a tangential entry of fluid to the middle region of the well whereby flow of fluid in the well is formed into a vortex which will tend to draw fluid from around the specimen without direct flow over the specimen.

7. Perfusion incubator apparatus comprising the assembly of claim 1 and further comprising an input arrangement for supplying the fluid to the said inlet, and an output arrangement for removing fluid from the outlet.

8. Apparatus according to claim 7, wherein the output arrangement has a pump for assisting with the removal of a substantially liquid fluid from the outlet.

9. Apparatus according to claim 8, wherein the pump is a peristaltic pump to provide a flow rate of fluid through each well of between 40 microliters per hour and 4000 microliters per hour when in flush mode.

10. Apparatus according to claim 9, further comprising a means for heating the fluid to a temperature of approximately 0.5° C. above the operating temperature of the well assembly.

11. Apparatus according to claim 7, further including an illumination device so that the specimen being cultured in the well assembly can be observed by means of a microscope, and further including a microscope mount for a microscope.

12. A method of operating the well assembly of claim 1, wherein the fluid is heated to a temperature approximately 0.5° C. above the operating temperature of the well before entering the fluid inlet, whereby gas bubbles are not formed in the culture well.

13. The well assembly of claim 1, wherein the fluid inlet and the fluid outlet are substantially parallel.

14. The well assembly of claim 1, further comprising a living cell in the lower section of the well.

15. The assembly of claim 1, where the fluid inlet and the fluid outlet are separate.

16. An incubator, including means for supplying fluid to the incubator, at least one well assembly and a well assembly heating unit, a peristaltic pump and a fluid collection unit, the well assembly including a plurality of wells, each having a fluid inlet and a fluid outlet, each fluid inlet being positioned generally in a midsection in the well and each fluid outlet being positioned above its respective fluid inlet, with the cell to be cultured to be positioned in a lower section of the well, the fluid inlet connected to the fluid supply and the fluid outlet connected to the fluid collection unit via the peristaltic pump whereby on the placing of a cell to be cultured in each well and flowing fluid through the well, culturing of the cell can occur.

17. A method of incubating a cell specimen in a well assembly, the well assembly having a lower section of a smaller diameter than an upper section, comprising the steps of placing the cell specimen in a lower section of a well of the well assembly;

introducing fluid into the well from an inlet above the cell specimen;

removing fluid from the well via an outlet, wherein the outlet is positioned above the inlet; and causing the fluid to flow in a vortex about the cell specimen without direct flow over the cell specimen.

18. The method according to claim 17, further including conditioning the fluid to a selected temperature slightly above an operating temperature of the well assembly, whereby the increased in solubility of gases in the fluid upon entry into the well assembly, and decrease in solubility because of suction that removes the fluid from the well assembly, are both compensated for preventing formation of gas bubbles in the well assembly.

* * * * *